(12) United States Patent
Horn et al.

(10) Patent No.: US 10,028,930 B2
(45) Date of Patent: Jul. 24, 2018

(54) COMPOSITIONS CAPABLE OF ENHANCING THERMOGENESIS AND USES THEREOF

(71) Applicant: Specialty Nutrition Group, Inc., Lighthouse Point, FL (US)

(72) Inventors: Gregory T. Horn, Lighthouse Point, FL (US); Susan Trimbo, Boca Raton, FL (US)

(73) Assignee: SPECIALTY NUTRITION CONSULTING, INC., Lighthouse Point, FL (US)

( * ) Notice: Subject to any disclaimer, the term of this patent is extended or adjusted under 35 U.S.C. 154(b) by 51 days.

(21) Appl. No.: 15/022,543

(22) PCT Filed: Sep. 15, 2014

(86) PCT No.: PCT/US2014/055620
§ 371 (c)(1),
(2) Date: Mar. 16, 2016

(87) PCT Pub. No.: WO2015/041977
PCT Pub. Date: Mar. 26, 2015

(65) Prior Publication Data
US 2016/0228400 A1 Aug. 11, 2016

Related U.S. Application Data

(60) Provisional application No. 61/878,870, filed on Sep. 17, 2013.

(51) Int. Cl.
| | | |
|---|---|---|
| *A61K 36/00* | (2006.01) | |
| *A61K 31/336* | (2006.01) | |
| *A61K 39/00* | (2006.01) | |
| *A61K 9/20* | (2006.01) | |
| *A61K 31/4745* | (2006.01) | |
| *A61K 31/522* | (2006.01) | |
| *A61K 36/17* | (2006.01) | |

(52) U.S. Cl.
CPC .......... *A61K 31/336* (2013.01); *A61K 9/2086* (2013.01); *A61K 31/4745* (2013.01); *A61K 31/522* (2013.01); *A61K 36/17* (2013.01); *A61K 39/0001* (2013.01)

(58) Field of Classification Search
CPC ..................................................... A61K 36/00
See application file for complete search history.

(56) References Cited

U.S. PATENT DOCUMENTS

| | | | |
|---|---|---|---|
| 6,399,089 B1 | 6/2002 | Yegorova et al. | |
| 2001/0043957 A1 | 11/2001 | Mann | |
| 2003/0215531 A1* | 11/2003 | Stogniew | A61K 36/75 424/730 |
| 2007/0116840 A1 | 5/2007 | Prakash et al. | |
| 2012/0128800 A1* | 5/2012 | Romero | A61K 31/35 424/729 |
| 2012/0231098 A1 | 9/2012 | Turano et al. | |

FOREIGN PATENT DOCUMENTS

WO 2013133903 A1 9/2013

OTHER PUBLICATIONS

PCT, International Search Report dated Dec. 23, 2014, issued during the prosecution of corresponding PCT International Patent Application No. PCT/US2014/055620.
Weiqi Ling et al., "A Causal Relationship Between the Neurotherapeutic Effects of miR182/7a and Decreased Expression of PRDM5"; Biochemical and Biophysical Research Communications 490 (2017); pp. 1-7.
A. E. Jeukendrup et al., "Fat Burners: Nutrition Supplements that Increase Fat Metabolism"; Supplement: Fat Metabolism, Key Papers from a Meeting organized by the Product Research Group of Lucozade Sport; International Association for the Study of Obesity 12, Obesity Reviews (2011), pp. 841-851.
CN Boozer et al., "Herbal Ephedra/Caffeine for Weight Loss: A 6-Month Randomized Safety and Efficacy Trial"; International Journal of Obesity (2002) 25, Nature Publishing Group, pp. 593-604.
Frank L. Greenway et al., "Effect of a Dietary Herbal Supplement Containing Caffeine and Ephedra on Weight, Metabolic Rate, and Body Composition", Obesity Research, vol. 12 No. 7, Jul. 2004; pp. 1152-1157.
A.G. Dulloo et al., "Normal Caffeine Consumption: Influence on Thermogenesis and Daily Energy Expenditure in Lean and Postobese Human Volunteers", The American Journal of Clinical Nutrition 1989, 49; pp. 44-50.
R.M. Hackman et al., "Multinutrient Supplement Containing Ephedra and Caffeine Causes Weight Loss and Improves Metabolic Risk Factors in Obese Women: A Randomized Controlled Trial", International Journal of Obesity (2006) 30, pp. 1545-1556.
Arne Astrup et al., "Caffeine: A Double-Blind, Placebo-Controlled Study of its Thermogenic, Metabolic, and Cardiovascular Effects in Healthy Volunteers", The American Journal of Clinical Nutrition 1990, 50; pp. 759-767.
Shirin Hasani-Ranjbar et al., "A Systematic Review of the Efficacy and Safety of Herbal Medicines used in the Treatment of Obesity", World Journal Gastroenterol, Jul. 7, 2009, 15(25), pp. 3073-3085.
Phil B. Fontanarosa, Md., et al., "The Need for Regulation of Dietary Supplements—Lessons from Ephedra", JAMA, Mar. 26, 2003, vol. 289 No. 12, American Medical Association, pp. 1568-1570.

(Continued)

*Primary Examiner* — Qiuwen Mi
(74) *Attorney, Agent, or Firm* — Lewis Brisbois Bisgaard & Smith LLP; Howard M. Gitten

(57) ABSTRACT

The present invention refers to novel compositions and to methods of using the compositions to treat and/or prevent obesity, obesity-related diseases or disorders (e.g., hyperglycemia, hyperinsulinemia, elevated hemoglobin A1c (HbA1c), diabetes, or cardiovascular disease), and overweight. This invention also generally relates to compositions and to methods of using the compositions to increase basal metabolic rate.

4 Claims, No Drawings

(56) References Cited

OTHER PUBLICATIONS

Kazuo Miyashita et al., "The Allenic Carotenoid Fucoxanthin, a Novel Marine Nutraceutical From Brown Seaweeds", Journal of SCI Food Agric. 2011, 91, Society of Chemical Industry—wileyonlinelibrary.com/jsfa; pp. 1166-1174.

M. Abodov et al., The Effects of Xanthigen(TM) in the Weight Management of Obese Premenopausal Women with Non-Alcoholic Fatty Liver Disease and Normal Liver Fat, Diabetes, Obesity and Metabolism 12, 2010, pp. 72-81.

Juan Peng et al., "Fucoxanthin, a Marine Carotenoid Present in Brown Seaweeds and Diatoms: Metabolism and Bioactivibes Relevant to Human Health", Marine Drugs 2011, 9, pp. 1806-1828.

Kristel Diepvens et al., "Obesity and Thermogenesis Related to the Consumption of Caffeine, Ephedrine, Capsaicin, and Green Tea", Am. J. Physiol. Regul Integr Comp Physiol 292, 2007, pp. R77-R85.

A.G. Dulloo et al., "Potentiation of the Thermogenic Antiobesity Effects of Ephedrine by Dietary Methylxanthines: Adenosine Antagonism or Phosphodiesterase Inhibition", Metabolism, vol. 41, No. 11 (Nov.), 1992; pp. 1233-1241.

Paul G. Shekelle et al., "Efficacy and Safety of Ephedra and Ephedrine for Weight Loss and Athletic Performance, A Meta-analysis", American Medical Association, Mar. 26, 2003, vol. 289, No. 12; pp. 1537-1545.

\* cited by examiner

COMPOSITIONS CAPABLE OF ENHANCING THERMOGENESIS AND USES THEREOF

CROSS REFERENCE TO RELATED APPLICATIONS

This application is the national phase under 35 U.S.C. § 371 of PCT International Application No. PCT/US2014/055620, filed Sep. 15, 2014, which claims the benefit of and priority to U.S. Provisional Patent Application Ser. No. 61/878,870 filed Sep. 17, 2013. The entire contents of this patent application are hereby incorporated by reference herein.

CROSS REFERENCE TO RELATED APPLICATIONS

This application claims the benefit of and priority to U.S. Provisional Patent Application Ser. No. 61/878,870, filed Sep. 17, 2013. The entire contents of this patent application are hereby incorporated by reference herein.

BACKGROUND OF THE INVENTION

The condition of overweight and obesity is a significant health and economic problem around the world, especially evident in the United States. The Centers for Disease Control in its 2012 report, estimated that approximately 35.7% adults are obese; a similar prevalence of overweight has also been observed. Individuals possessing a Body Mass Index (BMI) of between 25 and 29.9 are considered overweight, while individuals with a BMI≥30 are considered obese. BMI is calculated by dividing the weight (kg) of an individual by the square of the individual's height (m) (i.e., BMI=weight (kg)/[height (m)$^2$). Overweight and Obesity are often associated with increases in cardiovascular and metabolic diseases which also have an enormous impact on morbidity and mortality.

Approaches to weight management currently include: pharmaceuticals (Alli/Orlistat), Belviq, Qsymia), bariatric surgery, behavior modification, exercise, calorie-controlled diets and dietary supplements. The approaches leverage a variety of biological mechanisms that regulate body weight. Management of weight using any of the current approaches is challenging in view of the multifactorial nature of the condition. Despite having an array of options available, it is clear that more effective therapies are needed, especially those that are compatible with dietary modification.

Some dietary supplements and pharmaceutical compositions aim to enhance thermogenesis (diet-induced thermogenesis) as one means of increasing energy expenditure and fat oxidation and ultimately promoting weight loss. The set of substances regarded as thermogenic includes: *ephedra* (ephedrine alkaloids), bitter orange (synephrine), capsicum, caffeine, EGCG (tea extracts), protein, pyruvate, and fucoxanthin. Some of those listed are also classified as stimulants, notably caffeine and *ephedra*. Non-stimulant thermogenic compounds generally exert their effects via other mechanisms without activation of the central nervous system. Jeukendrup and Randell (2011) and Hasani-Ranjbar et al (2009) have recently reviewed a number of the ingredients that boost metabolic activity [Jeukendrup, A and R Randell. Obes Rev. 2011 October; 12(10):841-51; Hasani-Ranjbar, S. et al. World J Gastroenterol. 2009. 15 (25): 3073-3085]. Diepvens et al (2007) have also reviewed the metabolic actions of a number of these compounds [Diepvens, K et al. Am J Physiol Regul Integr Comp Physiol 2007 292(1):R77-85].

While a number of products, mostly dietary supplements, have been marketed containing stimulant-based and non-stimulant based thermogenic agents separately, the literature is replete of any studies or products that take advantage of using combinations of components that enhance thermogenesis via different mechanisms (e.g., combining stimulant and non-stimulant thermogenic agents). Therefore, this invention describes compositions containing ingredients (example: fucoxanthin and caffeine) that combine stimulant and non-stimulant agents to synergistically enhance thermogenesis for addressing the unmet need of treating obesity and overweight.

COMPOUNDS OF THE INVENTION

The invention relates generally to compositions and to methods of using the compositions to treat and/or prevent obesity, obesity-related diseases or disorders (e.g., hyperglycemia, hyperinsulinemia, elevated hemoglobin A1c (HbA1c), diabetes, or cardiovascular disease), and overweight. This invention also generally relates to compositions and to methods of using the compositions to increase basal metabolic rate.

In one aspect, the invention provides a composition comprising at least two compounds capable of enhancing thermogenesis or identified as capable of enhancing thermogenesis, wherein at least one of said compounds is a non-stimulant. In another aspect, one of said components is a non-stimulant.

In another aspect, the invention provides a composition comprising a) fucoxanthin, b) a caffeine source, and c) *ephedra; ephedra* extract, or isolated component or components from *ephedra* extract; or ephedrine alkaloids from any source, natural or synthetic.

Ephedrine alkaloids, from synthetic sources or the botanical *Ephedra sinica*, exert their effects primarily by enhancing norepinephrine and epinephrine, which ultimately promotes weight loss [Dulloo A. Int J Obes Relat Metab Disord 1993 17 Suppl 1: S35-S40; Dulloo A et al. Metabolism 1992 41: 1233-1241]. A number of in vitro and animal studies have examined the biological actions of ephedrine alkaloids. More interesting and relevant are the human studies that have been performed. In a six month randomized, controlled trial examining the effect of an *ephedra*/caffeine combination, subjects lost 2.7 kg more weight and 1.7 kg more body fat than the placebo group [Boozer, C. et al. Int J Obes Relat Metab Disord 2002. 26 (5): 593-604]. Shekelle et al (2003) conducted a meta-analysis of studies examining the effect of *ephedra* and/or ephedrine on weight loss [Shekelle, P. JAMA. 2003. 289 (12): 1537-45]. *Ephedra* usage was associated with modest weight loss. Greenway et al (2004) found that *ephedra*, in combination with caffeine, promoted weight and fat loss with an 8% increase in resting metabolic rate, a gauge of thermogenesis [Greenway, F. Obes Res. 2004. 12(7): 1152-7]. Hackman et al. (2006) reported significant weight loss as well as improvement in metabolic risk factors in a group of premenopausal women taking an *ephedra* and caffeine combination product [Hackman, R. et al. Int J Obes. 2006. 30 (10): 1545-56].

Caffeine is a well-studied compound which affects thermogenesis by inhibiting the phosphodiesterase-induced degradation of intracellular cyclic AMP (cAMP). In addition, there is evidence for the metabolic response to caffeine from mechanisms involving catecholaminergic stimulation of adipocytes, stimulation of substrate cycles like the Cori cycle (conversion of glycogen and glucose to lactate), and the free fatty acid (FFA)-triglyceride cycle. Dulloo et al. (1989) noted the ability of caffeine to potentiate the thermogenic effect of ephedrine, especially under conditions of caloric restriction, likely via the inhibition of phosphodiesterase activity [Dulloo, A et al. Am J Clin Nutr 1989 49(1):44-50]. Astrup et al (1991) confirmed, in an acute dose clinical trial in healthy volunteers, that ephedrine plus caffeine was most effective in promoting thermogenesis [Astrup, A. et al. Am J Clin Nutr. 1990. 51 (5): 759-67].

Fucoxanthin is a carotenoid extracted from brown seaweed. Recent reviews on fucoxanthin note that the compound has a unique chemical structure that is undoubtedly responsible for its various metabolic activities [Peng, J et al. Mar. Drugs 2011. 9: 1806-28; Miyashita, K et al. J Sci Food Agric 2011 91 (7): 1166-74]. Preclinical research in rodents suggests that it exerts its thermogenic actions by inducing the expression of uncoupling proteins (UCP-1, UCP-2, UCP-3) that dissipate energy by affecting oxidative phosphorylation in brown and white adipose tissue [Maeda, H et al. Biochem Biophys Res Commun. 2005. 332 (2): 392-7]. Fucoxanthin has been shown to have a broad array of metabolic effects beyond UCP expression and it appears that the substance is an overall regulator of lipid metabolism in fat tissue. Fucoxanthin's effectiveness in weight regulation has been evaluated in humans [Abidov, M et al. Diabetes Obes Metabolism 2010. 12: 72-81]. In one 16 week double-blind, randomized, placebo-controlled study, Xanthigen-600/2.4 mg (300 mg PSO+300 mg brown seaweed extract containing 2.4 mg fucoxanthin) resulted in statistically significant reduction of body weight, waist circumference (Non-Alcoholic Fatty Liver Disease (NAFLD) group only), body and liver fat content, liver enzymes (NAFLD group only), serum triglycerides and C-reactive protein. Weight loss and reduction in body and liver fat content occurred earlier in patients with NLF than in patients with NAFLD. Fucoxanthin (>2.4 mg) and Xanthigen-400/1.6 mg (200 mg PSO+200 mg brown seaweed extract containing 1.6 mg fucoxanthin) significantly increased resting energy expenditure (REE) in NAFLD subjects compared to placebo. Xanthigen promoted weight loss, reduced body and liver fat content, and improved liver function tests in obese non-diabetic women. Xanthigen and Fucoxanthin also increased REE.

BRIEF DESCRIPTION OF THE INVENTION

In one aspect, the invention provides a composition comprising at least two compounds capable of enhancing thermogenesis or identified as capable of enhancing thermogenesis, wherein one of said compounds is a non-stimulant. In another aspect, the composition comprises one non-stimulant and at least one stimulant.

In any of the embodiments presented herein, a non-stimulant thermogenic agent is an agent selected from the group consisting of: a) fucoxanthin; b) branched-chain amino acid; c) decaffeinated tea, decaffeinated tea extract, or isolated component or components from decaffeinated tea; and d) capsaicin extract or isolated component or components from capsaicin extracts.

In any of the embodiments presented herein, a stimulant thermogenic agent is an agent selected from the group consisting of: a) a caffeine source; b) guarana; c) yerba mate; d) *ephedra*; e) *ephedra* extract, or isolated component or components from *ephedra* extract; and f) ephedrine alkaloids from any source, natural or synthetic.

In another aspect, the invention provides a composition comprising fucoxanthin and at least one compound selected of the group consisting of: a) a caffeine source; b) guarana; c) yerba mate; d) *ephedra*; e) *ephedra* extract, or isolated component or components from *ephedra* extract; and f) ephedrine alkaloids from any source, natural or synthetic.

In any of the embodiments presented herein, a caffeine source refers to a) caffeinated tea; b) caffeinated tea extract; c) isolated component or components from caffeinated tea; d) caffeine; or e) any combination of a)-d).

In another aspect, the invention provides a composition comprising fucoxanthin and a caffeine source. In another aspect, the composition further comprises berberine.

In any of the embodiments presented herein, any composition presented herein further comprises a) *ephedra*; b) *ephedra* extract, or isolated component or components from *ephedra* extract; or c) ephedrine alkaloids from any source, natural or synthetic.

In another aspect, the invention provides a composition comprising a) fucoxanthin, b) a caffeine source, and c) *ephedra*; *ephedra* extract, or isolated component or components from *ephedra* extract; or ephedrine alkaloids from any source, natural or synthetic. In another aspect, fucoxanthin is about 5-50 mg (preferably about 5 mg). In another aspect, the caffeine source comprises about 25-400 mg caffeine (preferably about 190 mg). In another aspect, the *ephedra*; *ephedra* extract, or isolated component or components from *ephedra* extract; or ephedrine alkaloids from any source, natural or synthetic comprises about 10-120 mg *ephedra* (preferably about 90 mg).

In any of the embodiments presented herein, any composition presented herein further comprises one or more compounds capable of increasing metabolic rate or identified as capable of increasing metabolic rate.

In any of the embodiments presented herein, a compound capable of increasing metabolic rate or identified as capable of increasing metabolic rate is selected from the group consisting of: a) cinnamon; b) bitter melon; c) long-chain omega-3 fatty acids or sources thereof; d) grape extracts; e) berberine; f) fenugreek; g) lycopene; and h) astaxanthin.

In any of the embodiments presented herein, any composition presented herein further comprises berberine.

In any of the embodiments presented herein, any of the compositions present herein may further comprise one or more of the group consisting of rosemary extract, oregano extract, apple cider vinegar powder, grape seed extract, broccoli juice concentrate, carrot juice concentrate, tomato juice concentrate, beet juice concentrate, spinach juice concentrate, cucumber juice concentrate, brussel sprout juice concentrate, cabbage juice concentrate, celery juice concentrate, kale juice concentrate, asparagus juice concentrate, green bell pepper juice concentrate, cauliflower juice concentrate, parsley juice concentrate, and wheat grass juice concentrate.

In another aspect, this invention relates to a multicomponent formula, where each component has thermogenic activity. The components each have a specific mode of action in the body, and their thermogenic effects are complimentary. The components each have their own characteristic bioavailability and metabolism. It is important to note that the compositions covered in this invention optimize effectiveness by combining components with complementary actions. Components of the formulas also have different pharmacokinetic properties. Combining select components enhances their overall effectiveness. Combining these components also allows one product to offer a broad approach to managing the complex inflammatory and/or oxidative stress responses.

In another aspect, the invention provides a method of treating hyperglycemia in a subject identified as suffering from hyperglycemia comprising the administration to said subject an effective amount of any composition presented herein, such that said hyperglycemia is improved. In another aspect, the hyperglycemia is identified in the subject using fasted or post-prandial glucose measurements.

In another aspect, the invention provides a method of treating hyperinsulinemia in a subject identified as suffering from hyperinsulinemia comprising the administration to said subject an effective amount of any composition presented herein, such that said hyperinsulinemia is improved. In another aspect, the hyperinsulinemia is identified in the subject using fasted or post-prandial insulin measurements.

In another aspect, the invention provides a method of reducing elevated HbA1c levels in a subject identified as suffering from hyperglycemia comprising the administration to said subject an effective amount of any composition presented herein, such that said elevated HbA1c level is improved. In another aspect, the elevated HbA1c level is identified in the subject using fasted or post-prandial HbA1c measurements.

In another aspect, the invention provides a method of treating diabetes in a subject identified as suffering from diabetes comprising the administration to said subject an effective amount of any composition presented herein, such that said diabetes is improved. In another aspect, the diabetes is identified in the subject using fasted or post-prandial measurements. In another instance, the treatment of diabetes in said subject reduces one or more parameters selected from the group consisting of glucose levels, insulin levels, triglycerides, non-esterified free fatty acids (NEFAs), ROS levels, and HbA1c.

In another aspect, the invention provides a method of treating cardiovascular disease in a subject identified as suffering from cardiovascular disease comprising the administration to said subject an effective amount of any composition presented herein, such that said cardiovascular disease is improved. In another instance, the treatment of cardiovascular disease in said subject reduces one or more parameters selected from the group consisting of blood pressure, athlerosclerosis, platelet aggregation, total cholesterol levels, ROS levels, C-reactive protein, TNF, BMI, triglycerides, and LDL cholesterol levels.

In another aspect, the invention provides a method of treating a subject at risk of developing diabetes, said method comprising:
 a. identifying said subject as at risk of developing diabetes; and
 b. administering to said subject any composition presented herein.

In another aspect, the subject is identified at risk of developing diabetes through one or more of parameters selected from the group consisting of elevated glucose levels, elevated insulin levels, elevated HbA1c levels, elevated NEFAs, elevated triglycerides, and elevated BMI. In another aspect, the elevated glucose levels, elevated insulin levels, elevated HbA1c levels, elevated NEFAs, elevated triglycerides, or elevated BMI is identified in the subject using fasted or post-prandial measurements.

In another aspect, the invention provides a method of treating a subject at risk of developing cardiovascular disease, said method comprising:

a. identifying said subject as at risk of developing cardiovascular disease; and
 b. administering to said subject any composition presented herein.

In another aspect, the subject is identified at risk of developing cardiovascular disease through one or more of parameters selected from the group consisting of hypertension, elevated total cholesterol levels, elevated LDL cholesterol levels, low HDL cholesterol levels, elevated C-reactive protein levels, elevated TNF levels, elevated triglycerides, elevated BMI, and atherosclerosis.

In another aspect, the invention provides a method of treating overweight and/or obesity in a subject identified as suffering from overweight and/or obesity comprising the administration to said subject an effective amount of any composition presented herein, such that said overweight and/or obesity is improved. In another instance, the treatment of overweight and/or obesity in said subject affects one or more of the following parameters selected from the group consisting of: reducing body weight, reducing percent body fat, reducing BMI, reducing waist circumference, reducing hepatic fat content, reducing liver enzymes (e.g., ALT, AST), increasing resting energy expenditure, reducing fasting glucose levels, reducing post-prandial glucose levels, reducing fasting insulin levels, reducing post-prandial insulin levels, and reducing ROS levels. In another instance, the method of treating overweight and/or obesity in said subject further comprises administering to said subject a reduced calorie diet regimen.

In another aspect, the invention provides a method of raising basal metabolic rate in a subject comprising the administration to said subject an effective amount of any composition presented herein, such that said basal metabolic rate is raised.

In another aspect, the invention provides a method of increasing expression of uncoupling proteins in a subject comprising the administration to said subject an effective amount of any composition presented herein.

In another aspect, the invention provides a method of modulating lipid metabolism in adipocytes in a subject comprising the administration to said subject an effective amount of any composition presented herein. In another aspect, the modulation of said lipid metabolism is increasing lipid metabolism.

In certain embodiments, the subject is a mammal, preferably a primate or human.

In another embodiment, the invention provides a method as described above, wherein the effective amount of the compound or composition (e.g., any composition delineated herein) ranges from about 0.005 µg/kg to about 500 mg/kg, preferably about 0.1 mg/kg to about 500 mg/kg, more preferably about 10 mg/kg to about 500 mg/kg of body weight.

In other embodiments, the invention provides a method as described above wherein the effective amount of the compound or composition (e.g., any composition delineated herein) ranges from about 1.0 nM to about 500 µM. In another embodiment, the effective amount ranges from about 100 nM to about 100 µM.

In other embodiments, the invention provides a method as described above wherein the effective amount of the compound or composition (e.g., any composition delineated herein) ranges from about 0.1 mg/ml to about 1000 mg/ml. In certain embodiments, the effective amount ranges from about 1.0 mg/ml to about 500 mg/ml. In another embodiment, the effective amount ranges from about 1.0 mg/ml to about 100 mg/ml.

In another embodiment, the invention provides a method as described above, wherein the compound or composition (e.g., any composition delineated herein) is administered intravenously, intramuscularly, subcutaneously, intracerebroventricularly, orally or topically.

Another object of the present invention is the use of a compound or composition (e.g., any composition delineated herein) as described herein for use in the treatment and/or prevention of obesity, obesity-related diseases or disorders (e.g., hyperglycemia, hyperinsulinemia, elevated hemoglobin A1c (HbA1c), diabetes, or cardiovascular disease), and overweight.

In one aspect, the invention provides a kit comprising an effective amount of a compound or composition (e.g., any composition delineated herein), in unit dosage form, together with instructions for administering the compound to a subject suffering from or susceptible to an obesity, obesity-related diseases or disorders (e.g., hyperglycemia, hyperinsulinemia, elevated hemoglobin A1c (HbA1c), diabetes, or cardiovascular disease), and overweight.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

DETAILED DESCRIPTION

Definitions

In order that the invention may be more readily understood, certain terms are first defined here for convenience.

As used herein, the term "at risk" of developing a certain disease or disorder (e.g., diabetes or cardiovascular disease) encompasses possessing any risk factor, susceptibility, or predisposition of developing a certain disease.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression.

As used herein, "activating" encompasses permitting, increasing and enhancing progression.

As used herein, "enriched" encompasses greater or increased amounts of a material or desired or active compound or agent relative to its natural or other reference state.

As used herein, as "extract" is a preparation of constituents of a material (e.g., seaweed), including for example, solvent extracts, concentrated forms of said constituents, concentrated solvent extracts, isolated chemical compounds or mixtures thereof.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of compositions presented herein are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 μg/kg to about 1000 mg/kg, preferably about 0.1 mg/kg to about 1000 mg/kg, more preferably about 10 mg/kg to about 500 mg/kg of body weight. In other embodiments, the therapeutically effective amount may range from about 0.10 nM to about 500 μM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. It will also be appreciated that the effective dosage of a compound used for treatment may increase or decrease over the course of a particular treatment.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

Compounds of the Invention

Compounds (e.g., isolated compounds, compounds within extracts, compounds fractionated from extracts) of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jahnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

The present invention also contemplates solvates (e.g., hydrates) of a compound of herein, compositions thereof, and their use in the treatment and/or prevention of obesity, obesity-related diseases or disorders (e.g., hyperglycemia, hyperinsulinemia, elevated hemoglobin A1c (HbA1c), diabetes, or cardiovascular disease), and overweight. As used herein, "solvate" refers to the physical association of a compound of the invention with one or more solvent or water molecules, whether organic or inorganic. In certain instances, the solvate is capable of isolation, for example, when one or more solvate molecules are incorporated in the crystal lattice of the crystalline solid.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Pharmaceutical Compositions

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific organozinc compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragacanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

Topical administration of the pharmaceutical compositions of this invention is especially useful when the desired treatment involves areas or organs readily accessible by topical application. For topical application topically to the skin, the pharmaceutical composition should be formulated with a suitable ointment, lotion, or cream containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

For topical administration, the active compound(s), extracts, enriched extracts, or prodrug(s) can be formulated as solutions, gels, ointments, creams, suspensions, and the like.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The present invention will now be demonstrated using specific examples that are not to be construed as limiting.

Example 1: Composition Comprising Fucoxanthin and Caffeine

A composition containing fucoxanthin (200 mg brown seaweed extract, 5 mg fucoxanthin) and caffeine (200 mg) in a tablet to be taken 1-2 times daily with meals. The composition is in a tablet form prepared using excipients that permit rapid release of caffeine; the fat soluble seaweed extract is released within 1 hour and does not block the absorption of the stimulant components. All components are released and absorbed within 4 hours.

Example 2: Composition Comprising Fucoxanthin, *Ephedra*, and Caffeine

A composition containing fucoxanthin (400 mg brown seaweed concentrate), *ephedra* (75 mg ephedrine alkaloids) and caffeine (400 mg caffeine). The quantities are the daily total and should be administered in 2 divided doses in conjunction with a meal. The composition is in a tablet form prepared using excipients that permit rapid release of caffeine and *ephedra*; the fat soluble seaweed extract is released within 1 hour and does not block the absorption of the stimulant components. All components are released and absorbed within 4 hours.

Example 3: Composition Comprising Fucoxanthin and Caffeine in a Bilayer Tablet A composition containing fucoxanthin (200 mg brown seaweed extract, 5 mg fucoxanthin) and caffeine (200 mg) in a bilayer tablet to be taken 1-2 times daily with meals. The composition is in a bilayer tablet form prepared using excipients where each layer is released at separate times but within 1 hour of each other with full release occurring by 3 hours.

Example 4: Composition Comprising Fucoxanthin, Berberine, and Caffeine

A composition containing fucoxanthin (400 mg brown seaweed concentrate), berberine (500 mg (500-1500 mg/d range)) and caffeine (400 mg caffeine). The quantities are the daily total and should be administered in 2 divided doses in conjunction with a meal. The composition is in a tablet form prepared using excipients that permit rapid release of caffeine; the fat soluble seaweed extract is released within 1 hour and does not block the absorption of the stimulant components. All components are released and absorbed within 4 hours.

Example 5: Composition Comprising Fucoxanthin and Caffeine Administered to Obese and/or Overweight Subjects A composition according to Example 1 can be administered to overweight or obese adults for 12 weeks. This treatment regimen increases energy expenditure and promotes weight loss in a manner beyond the effects of the individual components.

Example 6: Composition Comprising Fucoxanthin, *Ephedra*, and Caffeine Administered to Obese and/or Overweight Subjects A composition according to Example 2 can be administered to overweight or obese adults for 12 weeks. This treatment regimen increases energy expenditure and promotes weight loss in a manner beyond the effects of the individual components.

Example 7: Composition Comprising Fucoxanthin, Berberine, and Caffeine Administered to Obese and/or Overweight Subjects A composition according to Example 4 can be administered to overweight or obese adults for 12 weeks. This treatment regimen increases energy expenditure and promotes weight loss in a manner beyond the effects of the individual components.

Example 7: Composition Comprising Fucoxanthin, Berberine, and Caffeine Administered to Obese and/or Overweight Subjects in Conjunction With a Low Calorie Diet Regiment A composition according to Example 4 can be administered to overweight or obese adults for 12 weeks in conjunction with a low calorie diet regimen. This treatment regimen increases energy expenditure and promotes weight loss in a manner beyond the effects of the individual components.

All patents, patent applications, and published references cited herein are hereby incorporated by reference in their entirety.

While this invention has been particularly illustrated and described with reference to particular examples, it will be understood by those skilled in the art that various changes in form and details may be made therein without departing from the scope and spirit of the invention encompassed by the appended claims.

What is claimed is:

1. A composition comprising an effective amount of at least two compounds capable of enhancing thermogenesis or identified as capable of enhancing thermogenesis, wherein said at least two compounds comprise a non-stimulant fucoxanthin and stimulant a caffeine source, said composition further comprises an effective amount of a compound selected from the group consisting of: a) *ephedra*; b) *ephedra* extract, or isolated component or components from *ephedra* extract; or c) ephedrine alkaloids from any source, natural or synthetic.

2. The composition of claim 1, wherein:
   a. fucoxanthin is about 5-50 mg;
   b. caffeine source comprises about 25-400 mg caffeine; and
   c. *ephedra*; *ephedra* extract, or isolated component or components from *ephedra* extract; or ephedrine alkaloids from any source, natural or synthetic comprises about 10-120 mg ephedrine alkaloids.

3. The composition of claim 2, wherein:
   a. fucoxanthin is about 5 mg;
   b. caffeine source comprises about 190 mg caffeine; and
   c. *ephedra*; *ephedra* extract, or isolated component or components from *ephedra* extract; or ephedrine alkaloids from any source, natural or synthetic comprises about 90 mg ephedrine alkaloids.

4. The composition of claim 1, wherein said caffeine source comprises: a) caffeinated tea; b) caffeinated tea extract; c) isolated component or components from caffeinated tea; d) caffeine; or e) any combination of a)-d).

* * * * *